United States Patent [19]
Kolesa et al.

[11] Patent Number: 5,609,601
[45] Date of Patent: Mar. 11, 1997

[54] ENDOSCOPIC SURGICAL APPARATUS WITH ROTATION LOCK

[75] Inventors: Michael S. Kolesa, Norwalk; Ernie Aranyi, Easton, both of Conn.; Gary S. Kappel, Waltham, Mass.

[73] Assignee: United States Surgical Corporation, Norwalk, Conn.

[21] Appl. No.: 311,493

[22] Filed: Sep. 23, 1994

[51] Int. Cl.$^6$ .................................................. A61B 17/00
[52] U.S. Cl. .......................... 606/170; 606/174; 606/205; 128/751
[58] Field of Search ............................. 606/51, 52, 167, 606/174, 205–211; 128/750–751

[56] References Cited

U.S. PATENT DOCUMENTS

| | | |
|---|---|---|
| 4,078,555 | 3/1978 | Takahashi . |
| 4,203,430 | 5/1980 | Takahashi . |
| 4,607,619 | 8/1986 | Seike et al. . |
| 4,617,914 | 10/1986 | Ueda . |
| 4,815,476 | 3/1989 | Clossick . |
| 5,014,685 | 5/1991 | Takahashi . |
| 5,174,300 | 12/1992 | Bales et al. . |
| 5,176,702 | 1/1993 | Bales et al. . |
| 5,195,506 | 3/1993 | Hulfish . |
| 5,209,747 | 5/1993 | Knoepfler . |
| 5,258,006 | 11/1993 | Rydell et al. . |
| 5,286,255 | 2/1994 | Weber . |
| 5,287,845 | 2/1994 | Faul et al. . |
| 5,330,502 | 7/1994 | Hassler et al. . |
| 5,334,198 | 8/1994 | Hart et al. . |

FOREIGN PATENT DOCUMENTS

| | | |
|---|---|---|
| 0543107 | 5/1993 | European Pat. Off. . |
| 2688398 | 9/1993 | France . |
| WO9315663 | 8/1993 | WIPO . |

Primary Examiner—Michael Powell Buiz
Assistant Examiner—William Lewis

[57] ABSTRACT

A surgical instrument is disclosed for use in a wide variety of roles including grasping, dissecting, clamping, or retracting materials or tissue during surgical procedures performed either in open surgery or within the abdominal cavity. The surgical instrument includes a handle portion, a tubular body portion extending from the handle portion and defining a longitudinal axis, and tool structure associated with a distal portion of the tubular body portion. A rotation assembly is provided for effectuating rotation of the tool structure about the longitudinal axis of the body portion. Rotation locking structure is provided to lock the rotation assembly at a predetermined orientation such that it cannot be rotated with respect to the handle.

23 Claims, 5 Drawing Sheets

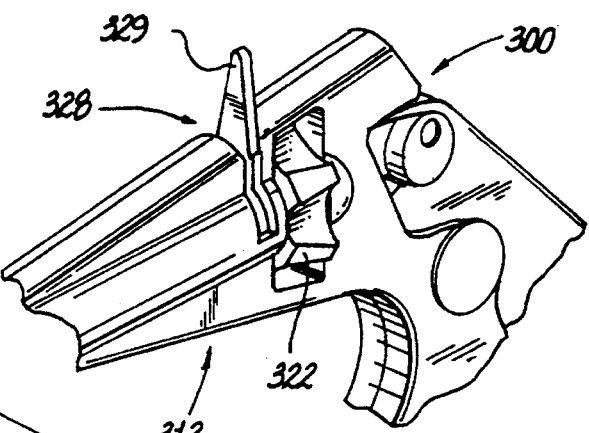
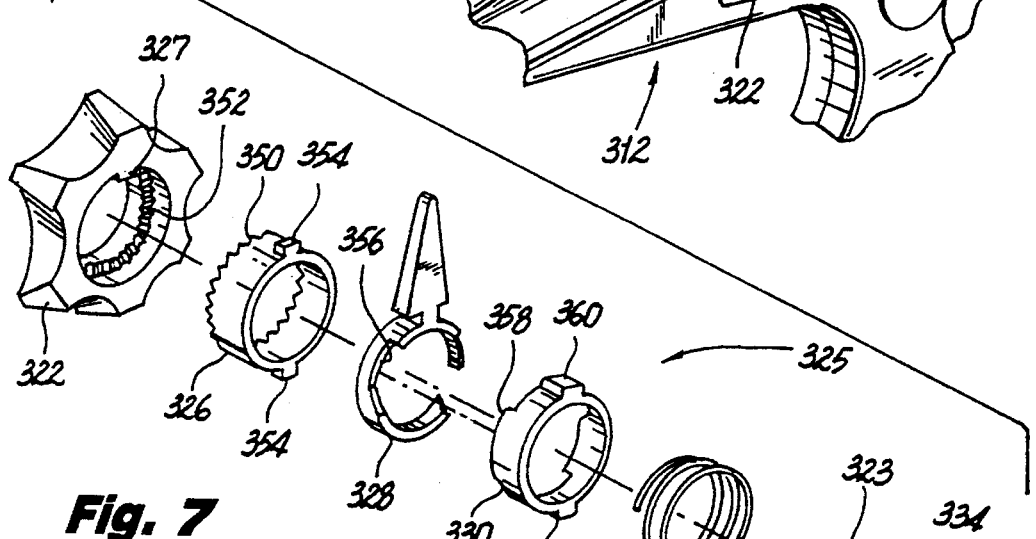
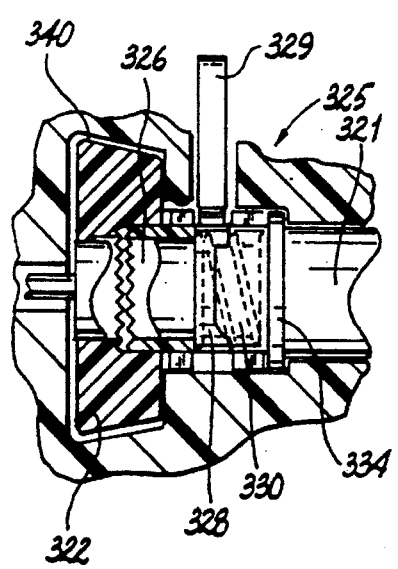
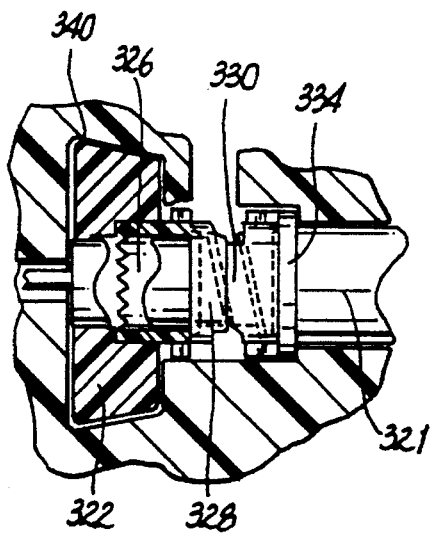

ENDOSCOPIC SURGICAL APPARATUS WITH ROTATION LOCK

BACKGROUND

1. Technical Field

This application relates to surgical apparatus, and more particularly to surgical apparatus having tool structure which can be rotated about a longitudinal axis.

2. Background of Related Art

The function of engaging and deflecting tissue or organs has been conventionally performed by one of several methods. A retractor, ordinarily in the form of a broad paddle or multiple fingers attached to a handle, may carry out this task. See, for example, U.S. Pat. No. 3,467,079 (James). Alternatively, this function may be carried out with a clamp device to grasp and deflect tissue. In order to facilitate access to internal structures it is widely known in the art to provide surgical instruments with articulating, and more particularly, rotating tool portions. It is also well known to provide the rotational feature with detents or other engageable surfaces to provide positive engagement of the tool portion at discrete angular position and inhibit free rotation thereof. However, these rotation inhibiting mechanisms can be subject to disengagement and unintended rotation of the tool portion when attempting to manipulate resistant tissue structures or to lift heavy organs during surgical procedures may result.

Endoscopic or laparoscopic procedures overcome many of the drawbacks of conventional surgery, particularly the requirement of making large incisions, often through major muscle groups, in order to manipulate the instrumentation in the body cavity. In contrast, instruments for use in endoscopic procedures are characterized by the provision of an elongated cannula structure having a relatively small diameter with a proximal and distal end. The distal end is passed through the surrounding tissue into the body cavity via an incision in the body cavity. The cannula provides a conduit for insertion of surgical instrumentation. The smaller incisions necessary for these procedures allow for shorter patient recovery periods and require less anesthesia than conventional methods.

Endoscopic or laparoscopic procedures, while minimizing patient trauma, reduces access to internal organs and therefore requires surgical instruments with tool structure remotely actuatable from outside the body. Typically this remote actuation includes manipulation of tool structure as well as rotation and articulation thereof. Commonly assigned U.S. application Ser. No. 07/925,496 discloses a surgical instrument adapted for rotating and articulating the tool structure relative to the longitudinal axis thereof. In particular, the apparatus shows a mechanism for indexing rotation of the tool structure.

However, for a surgeon performing operative procedures with heavy or resistant tissue structures, sufficient stress on the tool portion may overcome the rotation indexing mechanism and result in unwanted rotation of the tool structure. Therefore, a position locking mechanism is desired to positively fix the angular position of the tool structure against unintended rotation with respect to the handle.

SUMMARY

A surgical instrument is disclosed for use in a wide variety of roles including grasping, dissecting, clamping, or retracting materials or tissue during surgical procedures performed either in open surgery or within the abdominal cavity.

The surgical instrument includes a handle portion, a tubular body portion extending from the handle portion and defining a longitudinal axis, and tool structure associated with a distal portion of the tubular body portion. A rotation assembly is provided for effectuating rotation of the tool structure about the longitudinal axis of the body portion. Rotation locking structure is provided to lock the rotation assembly at a predetermined orientation such that it cannot be rotated with respect to the handle.

Further features of the subject apparatus will become more readily apparent from the following detailed description taken in conjunction with accompanying drawings.

BRIEF DESCRIPTION OF THE DRAWINGS

Various embodiments are described herein with reference to the drawings, wherein:

FIG. 6 is a perspective view of the handle portion of a third embodiment of the subject apparatus;

FIG. 7 is an exploded view of the rotational locking mechanism of the surgical apparatus of FIG. 6;

FIG. 8 is an enlarged side elevational view in partial cross-section of the apparatus of FIG. 6 in an unlocked position; and FIG. 9 is an enlarged side elevational view in partial cross-section of the apparatus of FIG. 6 in a locked position.

DETAILED DESCRIPTION OF PREFERRED EMBODIMENTS

Figure 1:
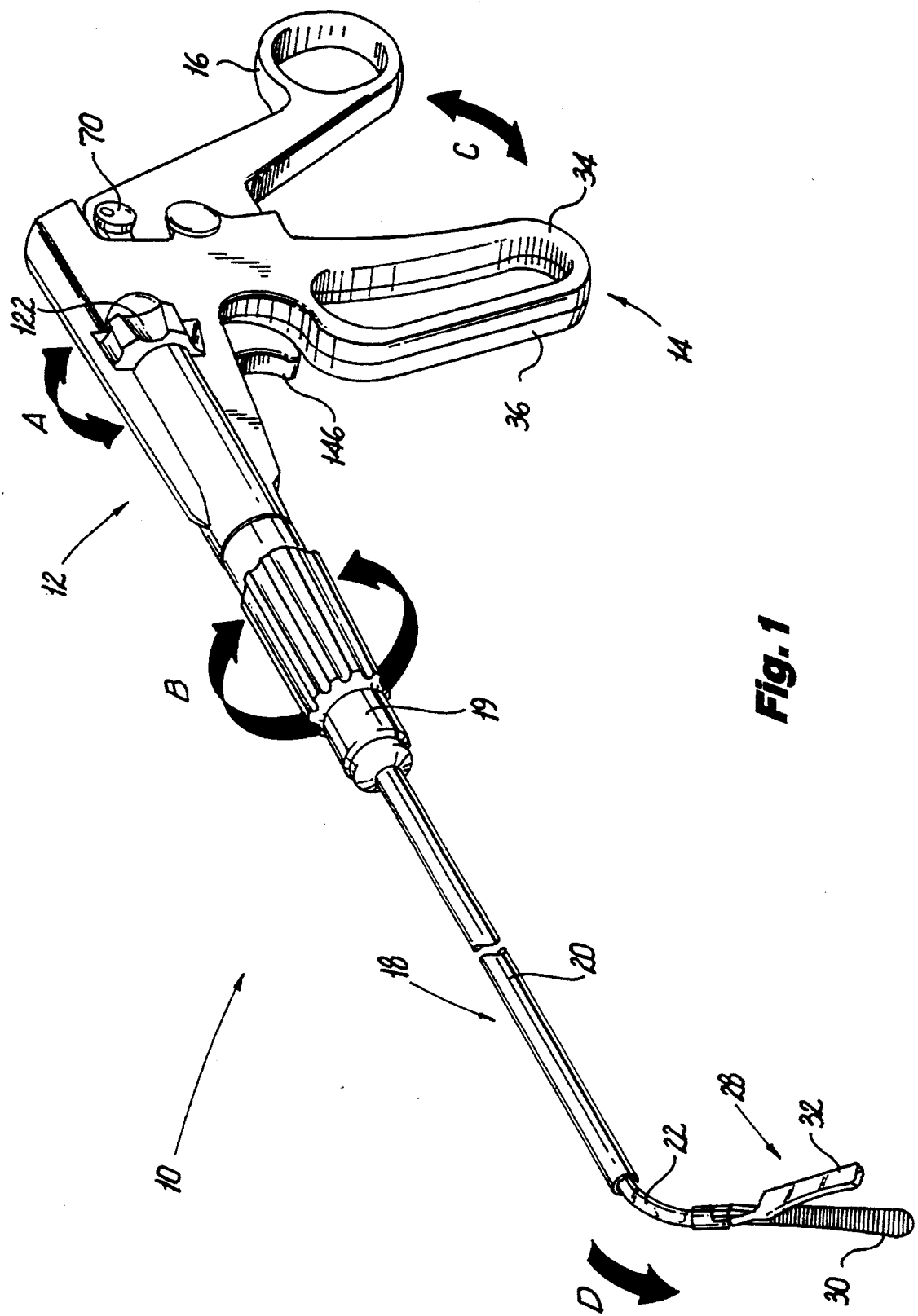
FIG. 1 is a perspective view of an endoscopic surgical instrument in accordance with a preferred embodiment of the subject apparatus.

In the drawings and in the description which follows, the term "proximal", as is traditional, will refer to the end of the apparatus which is closest to the operator, while the term "distal" will refer to the end which is furthest from the operator.

The present apparatus shall be discussed in terms of endoscopic procedures and apparatus. However, use herein of terms such as "endoscopic", should not be construed to limit the present application to an apparatus for use only in conjunction with an endoscopic tube. To the contrary, it is believed that the present apparatus may find use in conventional, open surgery as well as procedures where access is limited to a small incision including but not limited to arthroscopic or laparoscopic procedures.

A preferred surgical instrument is illustrated in FIG. 1 and is designated generally by reference numeral 10. Surgical instrument 10 includes a handle portion 12 including a fixed handle 14 with complementary sections 34 and 36, and a pivoting handle 16. An endoscopic portion 18 extends from handle portion 12 and includes an elongated tubular section 20 and an articulating section 22. Tool means, in this case tool structure 28 including cooperating jaws 30, 32, depends from the articulating section 22 and may be formed in a wide variety of configurations including graspers, dissectors, forceps, or clamps. Articulation means in the form of an axial drive screw assembly 19 causes translation of the tool structure 28. Rotation of the tool structure 28 is effectuated by rotation means herein shown as a rotatable collar 122 operatively associated with the handle portion 12. The mechanism for articulating the tool structure 28 and for operating the various configurations thereof is substantially disclosed in commonly assigned application Ser. No. 08/080,830 and is incorporated herein by reference. Although shown with an articulating tool structure, surgical instruments without this feature are also contemplated by this disclosure.

Figure 2:
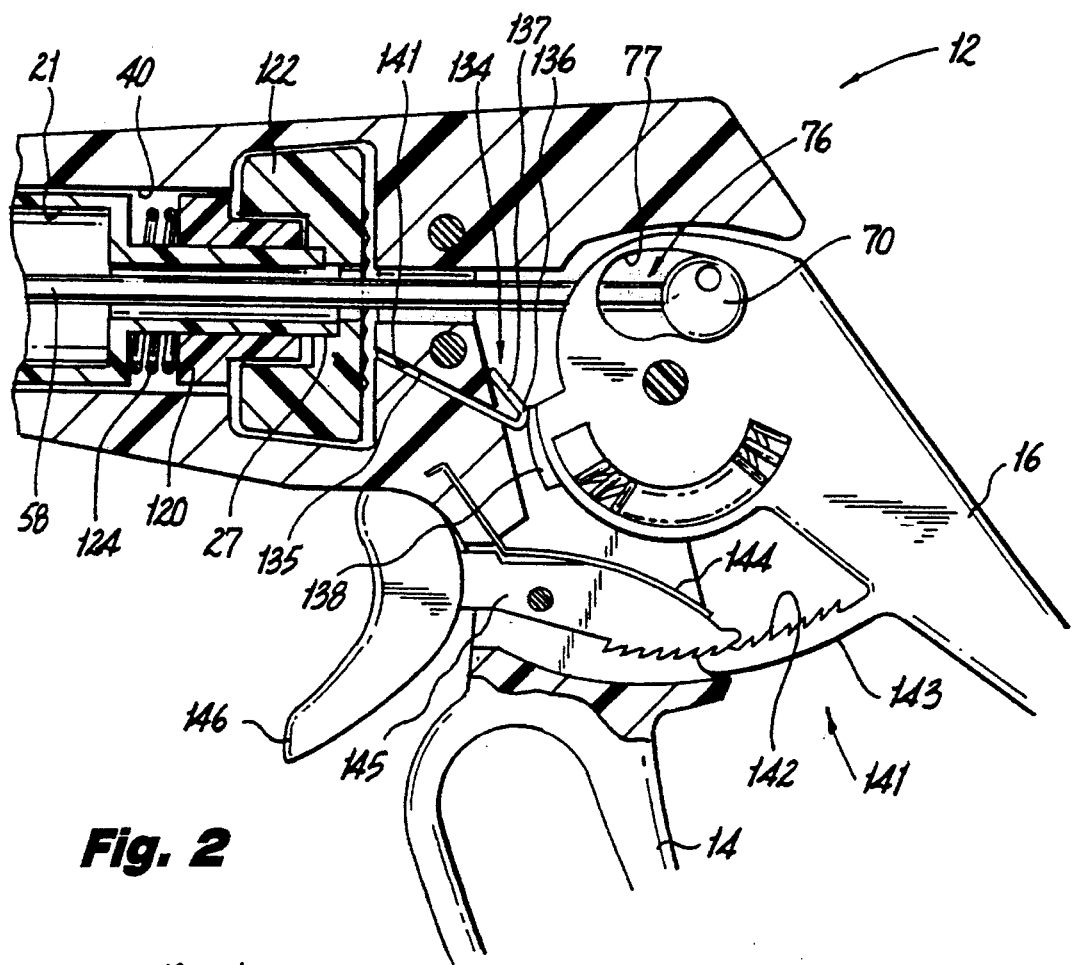
FIG. 2 is a cross-sectional view of the handle portion of the surgical instrument of FIG. 1 in an open position.
Figure 2A:
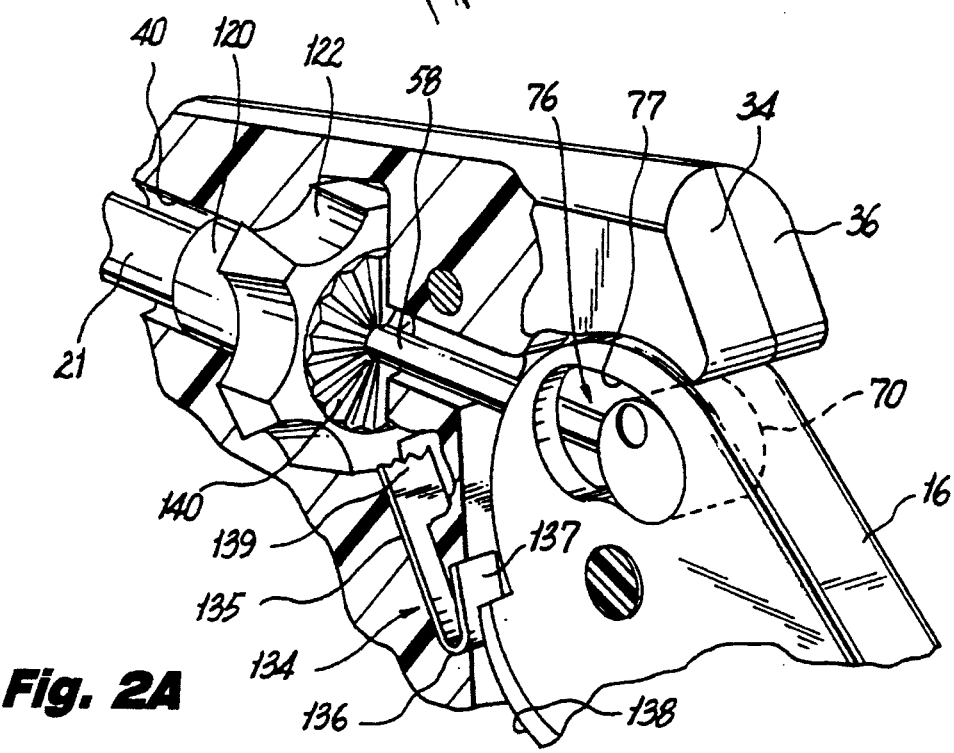
FIG. 2A is a perspective view in partial cross-section of the handle portion of the surgical instrument of FIG. 1 in an open position.
Figure 3:
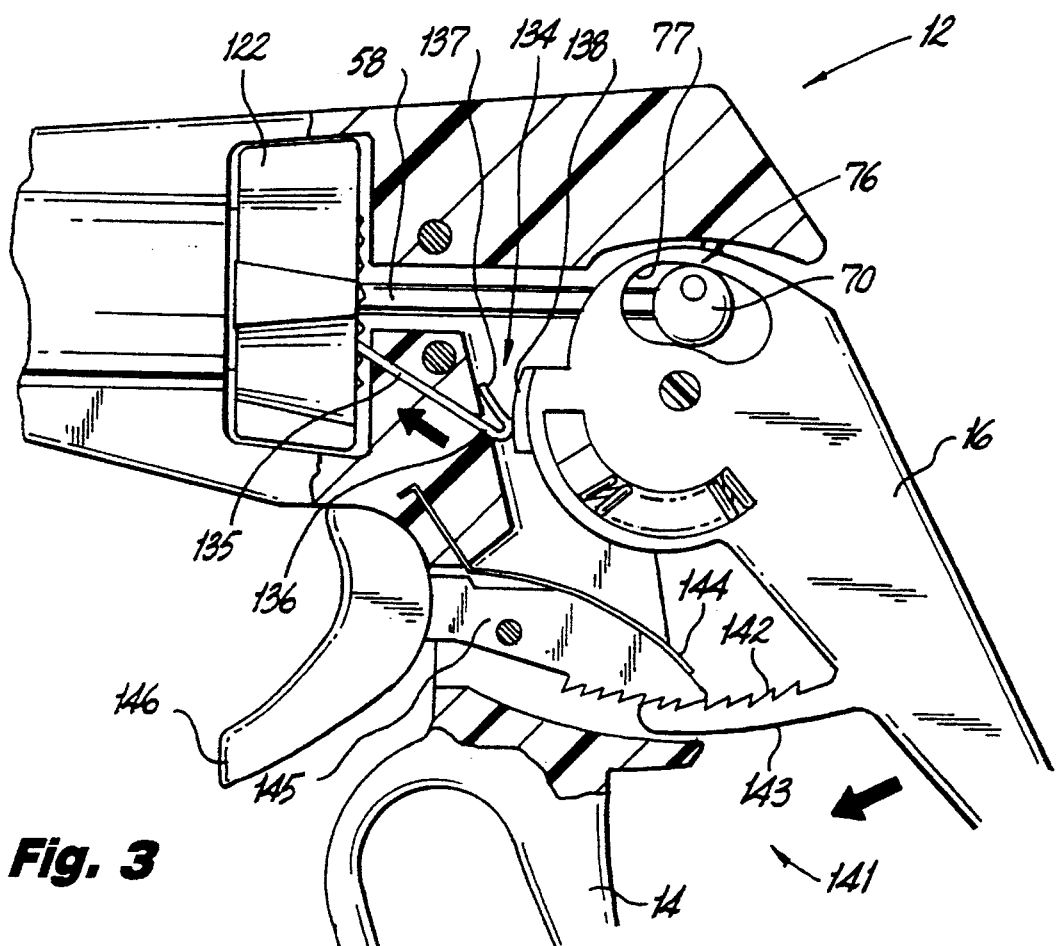
FIG. 3 is a cross-sectional view of the handle portion of the surgical instrument of FIG. 1 in a half closed position.
Figure 3A:
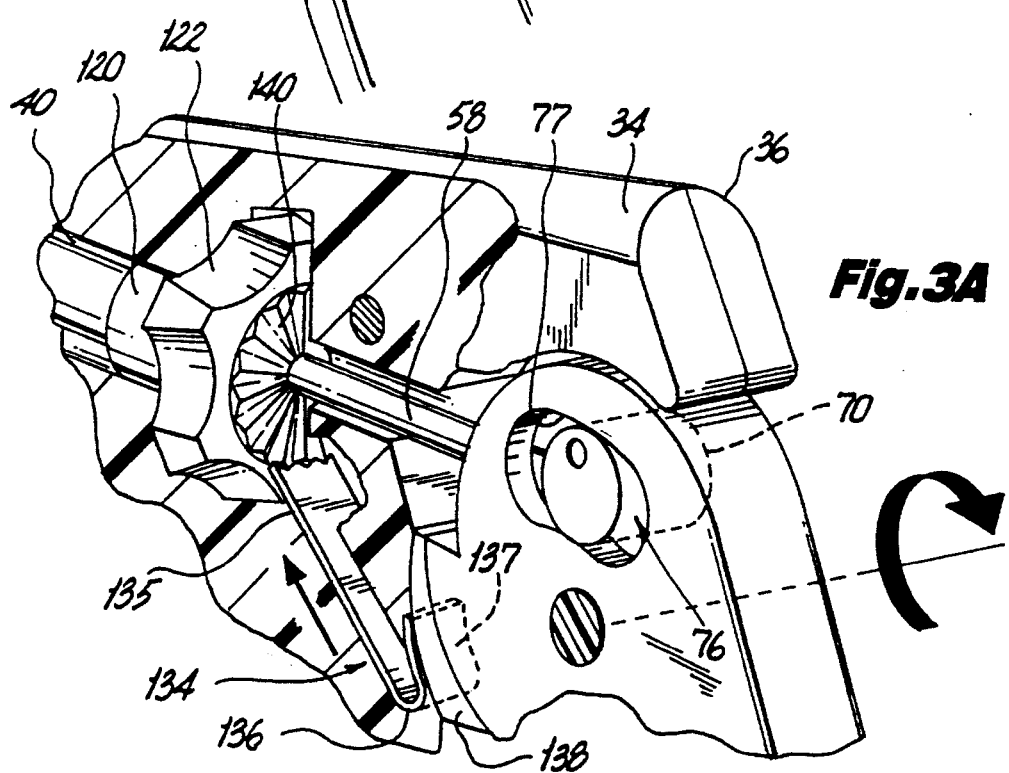
FIG. 3A is a perspective view in partial cross-section of the handle portion of the surgical instrument of FIG. 1 in a half closed position.

Referring now to FIGS. 2–3a, there is illustrated, in sequence, the relative movement of handles 14 and 16 from an open position to a partially closed position. As seen in FIGS. 2 and 2a, each of the complementary sections 34, 36 of handle portion 12 are formed with a portion of a stepped bore 40 which is provided therein for accommodating various components which will be described hereinbelow. A center rod member 58 having opposed proximal and distal ends is operatively associated at the distal end thereof to the tool structure 28. The proximal end of the center rod member 58 includes a head portion which is retained in a universal joint assembly 70. The universal joint assembly 70 is disposed within an elongate aperture 76 formed in the pivoting handle 16 of handle portion 12. The universal joint assembly 70 is adapted to slide within the elongate aperture 76 during a predetermined range of motion of the pivoting handle 16 with respect to the fixed handle 14. When the pivoting handle 16 is moved such that the edge of the elongate aperture 76 contacts the universal joint assembly 70, further closure of pivoting handle 16 will displace the universal joint assembly 70 and the center rod member 58 to actuate the tool structure 28.

With continued reference to FIGS. 2–2a, the endoscopic surgical instrument 10 further includes a mechanism for rotating the tool structure about its longitudinal axis relative to handle portion 12. This mechanism has an annular bushing 120 that is concentrically mounted within a rotatable collar 122 mounted within the stepped bore 40 formed in handle portion 12. Bushing 120 is maintained against collar 122 by a coiled spring 124 disposed in a section of bore 40. Spring 124 acts to bias bushing 120 toward the proximal end of the surgical instrument 10. The proximal end 27 of an inner tubular section 21 disposed within endoscopic portion 18 extends through bushing 120 and is mounted to rotatable collar 122 for rotation.

A distal end of inner tubular section 21 is operatively associated with the tool structure 28 such that axial rotation of the rotatable collar 122 will cause corresponding rotation of inner tubular section 21 to effectuate remote rotation of the tool structure 28 about the longitudinal axis defined by the elongated section 20 of surgical apparatus 10.

The endoscopic surgical instrument 10 further includes rotation locking means, in this case illustrated as a locking mechanism for locking the endoscopic portion 18 in a particular angular displacement with respect to the handle portion 12 by effectuating the pivoted handle 16. The locking mechanism includes a spring member 134 preferably formed of resilient sheet metal or similar material and having a first straight section 135, an acute angle elbow section 136, and a second straight section 137. The distal edge of the first section 135 is provided with teeth 139 designed to engage an annular ratchet 140 provided on a proximal face of the rotatable collar 122. The handle sections 34 and 36 are formed with a molded slot 14 1 adapted to permit slidable mounting of the spring 134, which is normally biased in a proximal position spaced from the rotatable collar 122 to permit unrestricted rotation thereof.

The pivoting handle 16 is provided at a distal portion thereof with a camming surface 138 having a pre-selected angle of incline portion. The camming surface 138 of the present embodiment is designed such that moving the pivoting handle 16 from an open position to about a half-closed position displaces the camming surface into abutment with the spring member 134 and further motion of the pivoting handle 16 drives the spring 138 against the bias into engagement with the annular ratchet 140 of the rotatable collar 122, thereby restricting angular displacement of the rotatable collar 122 and the associated endoscopic portion 18. One skilled in the art will appreciate that by varying either the angle of the incline portion of the cam or the position of the elongated slot, the point of engagement with the annular ratchet 140 can be changed.

The surgical instrument further includes an indexing mechanism to index movement of the pivoted handle 16 with the fixed handle 14. This permits progressive closure of the tool structures, for example, grasper jaws 30, 32 onto tissue as well as the application of uniform and predefined pressure thereon. The fixed handle is provided with a spring tab 149 slidable within an arcuate slot 147 formed in the pivoted handle 16. The spring tab 149 retains the distal end of a spring 148 disposed within the arcuate slot 147, thereby normally biasing the fixed handle 14 and the pivoted handle 16 in an open position corresponding to an open position of jaws 30, 32. (See, FIG. 1) The handle 12 is further provided with a double ratchet assembly 141 having a rack 143 with sloped notches 142 formed in the pivoted handle 16 and a pawl 145 is normally biased into engagement with the rack 142 by ratchet spring 144, inhibiting the pivoted handle 16 to open with respect to the fixed handle 14, and thereby maintaining the tool structure 28 in a fixed position. A trigger 146 is provided to pivot the pawl 145 against the ratchet spring bias out of engagement with the rack 142 to permit opening of the handle 12. By maintaining pressure on the trigger 146, unrestricted movement of the tool structure 28 is enabled.

In the open position illustrated in FIG. 2, pivoted handle 16 is fully extended with respect to fixed handle portion 14. In FIG. 2A, the camming surface 138 is disposed in its proximal-most position with respect to the spring 134, which remains in a normally biased position spaced proximally from the axial gearing 140 of the rotatable collar 122. The rotatable collar 122 is permitted unrestricted rotation within the stepped bore 40. In addition, in the open position the universal joint assembly 70 is disposed at the proximal portion of the elongate aperture 76.

FIGS. 3–3A illustrate the handle portion 12 of the surgical instrument 10 adjacent a half-closed position with respect to the fixed handle 12. In FIG. 3A, the camming surface contacts the proximal portion of the spring 134 and drives the spring 134 distally until the teeth 139 formed on the first portion of the spring 135 into engagement with the axial gearing 140, thereby inhibiting rotation of the collar 122 and associated tool structure 28. Although the camming surface 138 of the present embodiment is shaped to lock the rotatable collar 122 adjacent a half-closed position of the pivoted handle 16, surgical requirements may direct the preselected incline portion of the camming surface 138 to provide rotation lock at other relative positions of the pivoted handle 16, such as the beginning or end of the pivoted handle's range of motion.

Continuing with FIG. 3A, at the half-closed position the universal joint assembly 70 has moved within the elongate aperture 76 to the distal most edge 77 of the aperture 76. Further closing of the pivoted handle 16 will initiate contact between the distal most edge 77 of the aperture 76 and the universal joint assembly 70. Subsequent closure of the pivoted handle 16 will proximally displace the universal joint assembly 70 thereby pulling the center rod member 58 in a proximal direction and effectuating the tool structure 28.

Figure 4:
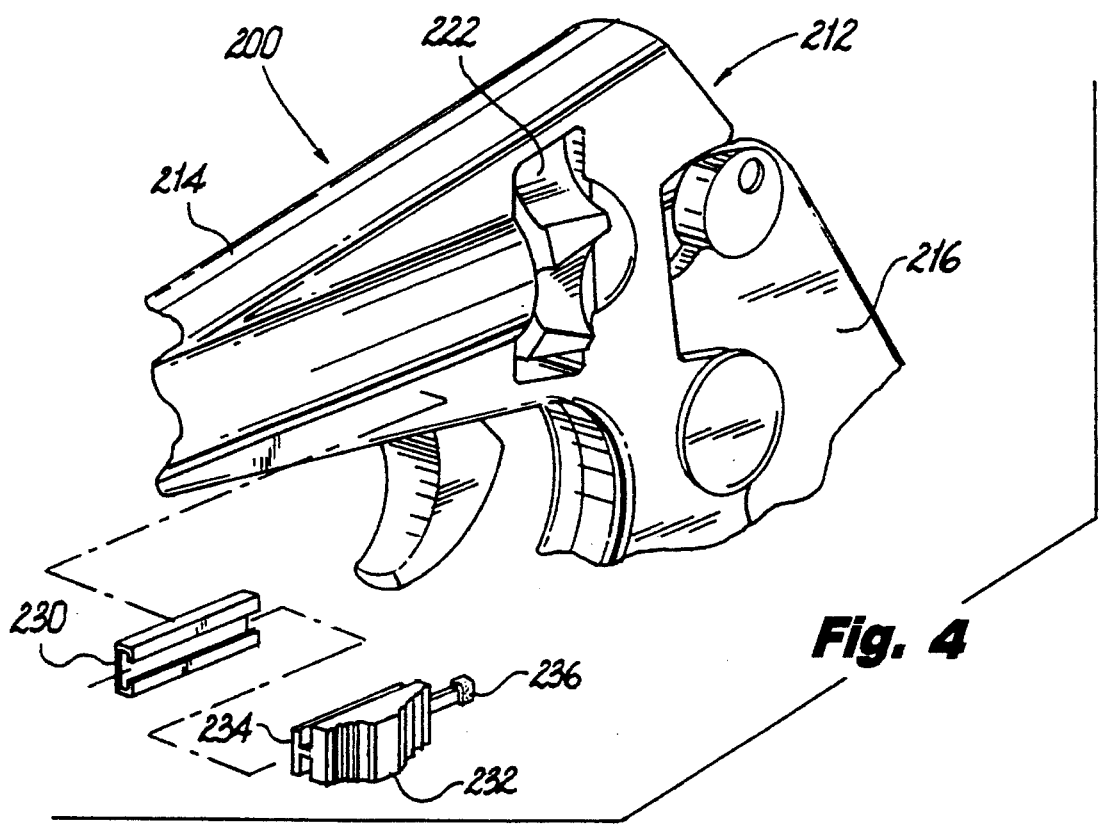
FIG. 4 is a perspective view of the handle portion of another embodiment of the subject apparatus.
Figure 5:
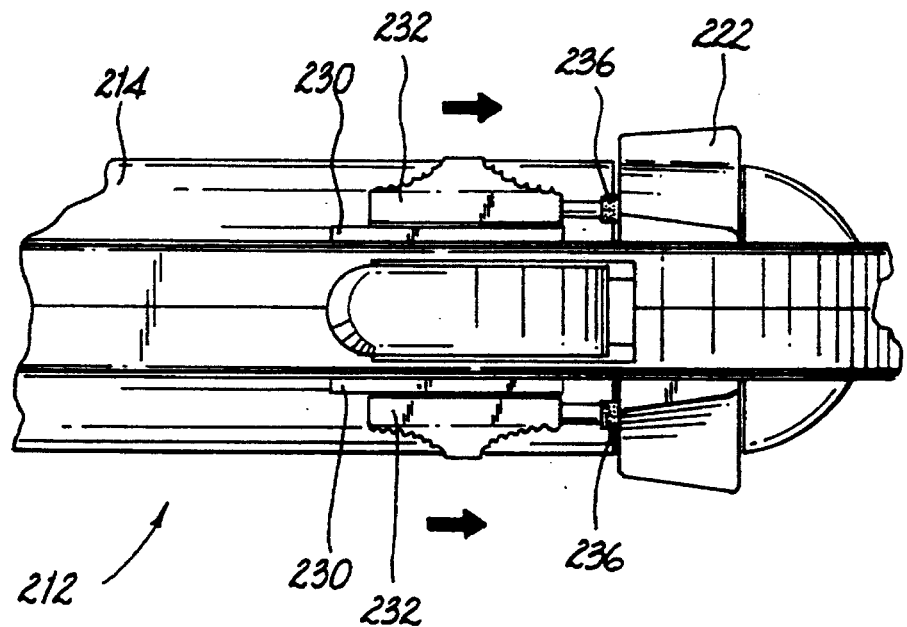
FIG. 5 is an elevational view of the embodiment of FIG. 4.

FIGS. 4–5 illustrate an alternate embodiment of the rotational locking assembly for the surgical instrument. Referring to FIG. 4, there is shown the handle portion 212 of the surgical apparatus 200. Rotation of the endoscopic portion 18 is effectuated by rotation of the rotatable collar 222 substantially as described above with regard to the surgical apparatus 10. At least one slide 230 is provided within the handle portion 214 distal the rotatable collar 222. Alternatively, a channel may be molded into the handle portion 214 itself. The slide is adapted to permit reciprocal longitudinal movement of a sliding member 232 having a flange 234 with a T-shaped cross-section to fit within the slide 230. The sliding member is further provided with a frictional tab 236 on a proximal portion thereof adapted for frictional engagement with the distal face of the rotatable collar 222. As best seen in FIG. 5, the sliding member 232 within the slide 230 is displaced longitudinally by the surgeon, whereupon the frictional tab 236 is driven into frictional engagement with the distal face of the rotatable collar 222, thereby positively locking the rotatable collar 222 against rotational movement with respect to the handle. The sliding member 232 may be provided with teeth to positively engage notches or gearing provided on the distal face of the rotatable collar 222 to improve locking engagement.

Referring now to FIGS. 6–9, there is illustrated another alternative embodiment of the surgical instrument designated generally by reference numeral 300. FIG. 6 illustrates the handle portion 312 of the alternative embodiment of the surgical apparatus 300. Rotation of an inner tubular section 321 is effectuated by a rotatable collar 322. A rotating lever 328 is provided with a lever handle 329 for locking rotational movement of the inner tubular section 321 with respect to the handle 312.

Referring now to FIG. 7, there is illustrated the components of the locking mechanism 325 of the alternative embodiment. The rotatable collar 322 is provided with a longitudinal bore to receive the proximal end of the tubular section 321. A slot 323 on the proximal portion of the inner tubular section 321 is adapted to fit within a tab 327 in the rotatable collar 322. As in the previous embodiments described above, the proximal portion of the inner tubular section 321 and the rotatable collar 322 are dimensioned for coaxial rotation within a longitudinal bore 340 in the handle portion 312. The locking mechanism 325 coaxially mounted distal of the rotatable collar 322, includes a cylindrical bushing 326, the rotating cam 328, a fixed cam 330 and a cylindrical spring 332. The bushing 326 is provided with a series of ratcheting structure 350 on the proximal surface adapted to engage an ratcheting structure 352 provided on a distal surface of the rotatable collar 322. The cylindrical spring 332 is coaxially mounted distal of the bushing 326 and is longitudinally retained at its distal end by an annular flange 334 on the proximal portion of tubular section 320. The spring 332 normally biases the ratcheting structure 350 into approximation but not engagement with the ratcheting structure 352 of the rotatable collar 322. A pair of bosses 354 on the bushing 326 are adapted to slide within a longitudinal groove provided within the longitudinal bore 340 to inhibit rotational movement of the bushing 326 within the bore 340.

With continued reference to FIG. 7, the rotating cam 328 and the fixed cam 330 are coaxially mounted distal of the bushing 326 and are sized to surround the cylindrical spring 332. The rotating cam 328 is provided with a pair of notches 356 on a distal surface designed to cooperate with a pair of camming surfaces 358 on a proximal surface of the fixed cam 330. The fixed cam 330 is further provided with bosses 360 adapted to fit within longitudinal grooves in the longitudinal bore 340 to inhibit rotational movement thereof.

Referring now to FIGS. 8–9, there is shown in sequence, the procedure for locking the rotatable collar 332 with respect to the handle portion 312. FIG. 8 illustrates the locking mechanism 325 in an unlocked position. When the lever handle 329 of the rotating cam 328 is in a first position, the notch 356 in the rotating cam 328 is in cooperation with the camming surface 358 of the fixed cam 330. The bushing 326 remains normally biased out of engagement with the rotating collar 322 to permit unrestricted rotation thereof.

FIG. 9 illustrates the locking mechanism 325 in a locked position. Angular displacement of the lever handle 329 to a second position disengages the rotating cam 328 from engagement with the camming surface 358 of the fixed cam 330, thereby displacing the rotating lever 326 proximally. Consequently the teeth 350 on the bushing 326 are driven by the rotating lever 328 into engagement with the ratcheting structure 352 of the rotatable collar 322, thereby inhibiting rotation thereof.

It will be understood that various modifications may be made to the embodiments disclosed herein. For example the locking mechanism described above may be utilized in conjunction with instruments used in conventional, open surgery. Or, for example, the locking mechanism described in the first embodiment may be used in conjunction with a universal joint which is adapted to rotate within a non-elongate aperture instead of an elongate aperture. Therefore, the above description should not be construed as limiting, but merely as exemplifications of preferred embodiments. Those skilled in the art will envision other modifications within the scope and spirit of the claims appended hereto.

What is claimed is:

1. A surgical apparatus comprising:

a handle portion;

a body portion extending from said handle portion and defining a longitudinal axis:

a tool structure connected to a distal portion of the tubular body portion, said tool structure being remotely operable from said handle portion;

a rotation assembly for effectuating remote rotation of the tool structure about the longitudinal axis of the body portion relative to the handle portion, said rotation assembly including an axially rotatable collar; and a rotation lock assembly movably mounted in said handle portion for movement between a locking position to lock the rotation assembly at a fixed angular position such that the rotation assembly cannot be rotated with respect to the handle portion and a disengaged position such that the rotation assembly can be freely rotated with respect to the handle portion.

2. A surgical apparatus of claim 1, wherein the rotation lock assembly comprises a resilient spring member normally biased in a configuration spaced from the rotating collar and actuated by movement of the handle portion to engage the rotatable collar to prevent rotation of the rotatable collar relative to the handle.

3. A surgical apparatus as recited in claim 1, wherein said rotation lock assembly comprises ratchet structure coaxial with the rotatable collar, the ratchet structure mounted for reciprocal longitudinal movement between an engaged position in restrictive engagement with the rotatable collar and a disengaged position out of engagement with said rotatable collar.

4. A surgical apparatus as recited in claim 3, wherein said ratchet structure further comprises:

a bushing coaxial with said rotatable collar and including first ratchet structure on a first end thereof, said bushing being mounted for translational movement between said engaged position in engagement with said rotatable collar and said disengaged position out of engagement with said rotatable collar; and cam structure including a fixed cam coaxially mounted with said rotatable collar, said fixed cam having a camming surface thereon, and a rotatable cam coaxially mounted in engagement with said fixed cam, said rotatable cam being rotatably movable between a first position wherein said fixed cam and said rotatable cam define a first longitudinal length and a second position wherein said fixed cam and said rotatable cam define a second elongated longitudinal length, said cam structure engaging said bushing such that when said rotatable cam is in said second position, said bushing is moved to said engaged position and when said rotatable cam is in said first position, said bushing is in said disengaged position.

5. A surgical apparatus as recited in claim 4, wherein said rotatable collar further includes second ratchet structure oriented coaxially to said first ratchet structure on said bushing.

6. A surgical apparatus comprising:

a handle portion having a fixed handle and a pivoting handle, the pivoting handle having a camming surface formed thereon;

an elongated portion depending from the handle portion, the elongated portion mounted for coaxial rotational movement independent of the handle portion;

a tool structure operatively connected adjacent a distal end portion of the elongated portion;

a rotatable collar engageable with the elongated portion for rotating the tool structure about the longitudinal axis of the elongated portion with respect to the handle portion; and a rotation lock assembly operatively associated with the camming surface of the pivoting handle to prevent rotation of the rotatable collar with respect to the handle portion.

7. A surgical apparatus of claim 6, wherein the rotation lock assembly comprises a resilient spring member normally biased in a configuration spaced from the rotating collar and actuated by the camming surface of the pivoting handle into abutment with the rotatable collar to prevent rotation of the rotatable collar relative to the handle.

8. A surgical apparatus as recited in claim 7, wherein the rotatable collar is provided with ratcheting structure.

9. A surgical apparatus as recited in claim 8, wherein the spring member is further provided with teeth adapted for engagement with the ratchet structure on the rotatable collar.

10. A surgical apparatus as recited in claim 6, wherein said tool structure is selected from the group consisting of graspers, dissectors, forceps and clamps.

11. A surgical apparatus as recited in claim 10, wherein the pivoting handle is normally biased in a position corresponding to an open position of said tool structure.

12. A surgical apparatus as recited in claim 6, wherein the handle portion is provided with an indexing mechanism for maintaining a predetermined relative position of the pivoting handle with respect to the fixed handle.

13. A surgical retractor as in claim 6, wherein said tool structure is articulatable relative to said elongate portion.

14. A surgical apparatus comprising:

a handle portion having a fixed handle and a pivoting handle defining an open and closed position, the fixed handle having a driving plunger assembly actuatable by the pivoting handle, the pivoting handle having an elongate aperture for enclosing a proximal end of said plunger assembly, said aperture configured and dimensioned to disengage actuation of the plunger by the pivoting handle during a predetermined translation of the pivoting handle, the pivoting handle having a camming surface thereon;

an elongated portion depending from the handle portion, the elongated portion mounted for coaxial rotational movement relative to said handle;

tool structure connected to a distal end portion of the endoscopic portion and operatively connected to the driving plunger assembly;

a rotation assembly adjacent the handle portion and the endoscopic portion for rotating tool structure about the longitudinal axis of the elongated portion, wherein the rotation assembly includes a coaxial rotatable collar member associated with the handle portion; and a rotation lock assembly operatively associated with the camming surface of the pivoting handle to prevent angular rotation of the rotatable collar with respect to the handle portion.

15. A surgical apparatus as recited in claim 14, wherein the rotation lock assembly comprises a resilient spring member normally biased in a configuration spaced from the rotating collar and actuated by the camming surface of the pivoting handle into abutment with the rotatable collar.

16. A surgical apparatus as recited in claim 15, wherein the rotating collar is provided with ratcheting structure, and wherein the spring member is further provided with teeth adapted for engagement with the ratcheting structure on the rotating collar.

17. A surgical apparatus as recited in claim 14, wherein said camming surface includes a predetermined incline portion which controls the relative position of said fixed handle and said pivoting handle wherein the rotation lock assembly is engaged with said rotation assembly.

18. Surgical retractor as recited in claim 17, wherein the incline portion is configured to restrain angular rotation of the rotatable collar at the half-closed position of the pivoting handle.

19. Surgical retractor as recited in claim 14, wherein the aperture in the pivoting handle is configured and dimensioned to disengage actuation of the driving plunger by the pivoting handle during actuation of the pivoting handle from the open position to a half-closed position, the pivoting handle actuating the piston from a half-closed position to a fully closed position.

20. A surgical apparatus comprising:

a handle portion;

a body portion extending from said handle portion and defining a longitudinal axis;

tool means connected to a distal portion of the tubular body portion and remotely actuable from said handle portion for manipulation of tissue;

rotation means for effecting remote rotation of the tool means about a longitudinal axis of the body portion relative to the handle portion; and rotation locking means movably mounted in said handle portion for movement between a locking position to lock the rotation means at a fixed position such that a rotation means cannot be rotated with respect to the handle portion and a disengaged position such that the rotation assembly can be freely rotated with respect to the handle portion.

21. A surgical apparatus as recited in claim 20, further comprising articulation means for articulating said tool means relative to said body portion.

22. A surgical apparatus as recited in claim 20, wherein said rotation means includes an axially rotatable collar.

23. A surgical apparatus of claim 22, wherein the rotation lock means comprises a resilient spring member normally biased in a configuration spaced from the rotating collar and actuated by the camming surface of the pivoting handle into abutment with a surface of the rotatable collar to prevent rotation of the rotatable collar relative to the handle.

\* \* \* \* \*